United States Patent [19]
Nelson

[11] Patent Number: 4,968,293
[45] Date of Patent: Nov. 6, 1990

[54] CIRCULATORY ASSIST DEVICE

[75] Inventor: Glen D. Nelson, Long Lake, Minn.

[73] Assignee: Medtronic, Inc., Minneapolis, Minn.

[21] Appl. No.: 325,711

[22] Filed: Mar. 20, 1989

[51] Int. Cl.$^5$ ............................................ A61N 1/362
[52] U.S. Cl. ......................................... 600/16; 623/3; 604/8
[58] Field of Search ...................... 604/8–10, 604/50; 600/16–18; 623/3, 900; 128/DIG. 3; 415/900

[56] References Cited

U.S. PATENT DOCUMENTS

| | | | |
|---|---|---|---|
| 3,771,899 | 11/1973 | Brumfield | 415/900 X |
| 3,966,358 | 6/1976 | Heimes et al. | 417/12 |
| 4,105,016 | 8/1978 | Donovan, Jr. | 128/1 D |
| 4,176,411 | 12/1979 | Runge | 623/3 |
| 4,411,268 | 10/1983 | Cox | 128/421 |
| 4,652,265 | 3/1987 | McDougall | 623/3 |
| 4,666,443 | 5/1987 | Portner | 623/3 |
| 4,813,952 | 3/1989 | Khalafalla | 623/3 |
| 4,820,300 | 4/1989 | Pierce et al. | 623/3 |

FOREIGN PATENT DOCUMENTS 8700420  1/1987  PCT Int'l Appl. ................... 600/17

OTHER PUBLICATIONS

*A Compact, Low Homolysis Non-Thrombogenic System for Non-Thoracotomy prolonged Left Vertricular Bypass,* Bernstein, E. F., et al. Trans. Amer. Soc. Artif. Int. Organs, vol. XX, 1974, pp. 643–654.

Article entitled "Muscle Energy for Total Artificial Heart Drive", by Thoma et al, published in *Artificial Organs,* vol. 5 (Suppl), 1981, pp. 441–445.

Article entitled "Left Ventricular Assistance in Dogs Using a Skeletal Muscle Powered Device for Diastolic Augmentation", by Neilson et al. published in *Heart Transplantation,* vol. IV, No. 3, May 1985, pp.343–347.

Article entitled "Effect of Electrical Stimulation on Diaphragmatic Muscle Used to Enlarge Right Ventricle", by Macoviak et al, published in *Surgery,* Aug. 1981, pp. 271–277.

Article entitled "Biophysical Studies on Nerve and Muscle", *Biophysics: Concepts and Mechanisms,* New York, Reinhold Pub., 1962, pp. 262–294.

Article entitled "Graft of the Diaphragm as a Functioning for the Myocardium", by Nakamura et al, published in the *The Journal of Surgical Research,* vol. IV, No. 10, Oct. 1964, pp. 435–439.

Article entitled "Synchronously Stimulated Skeletal Muscle Graft for Myocardial Repair", by Dewar et al, published in *The Journal of Thoracic and Cardiovascular Surgery,* vol. 87, No. 3, Mar. 1984, pp. 325–331.

*Primary Examiner*—John D. Yasko
*Assistant Examiner*—Adam J. Cermak
*Attorney, Agent, or Firm*—Robert J. Klepinski; S. A. Kassatly

[57] ABSTRACT

An assist device for the heart comprises a continuous flow pump for moving blood through a vessel and a muscle powered device for supplying pulsatility to the flow of blood, to simulate human heart pumping action.

9 Claims, 1 Drawing Sheet

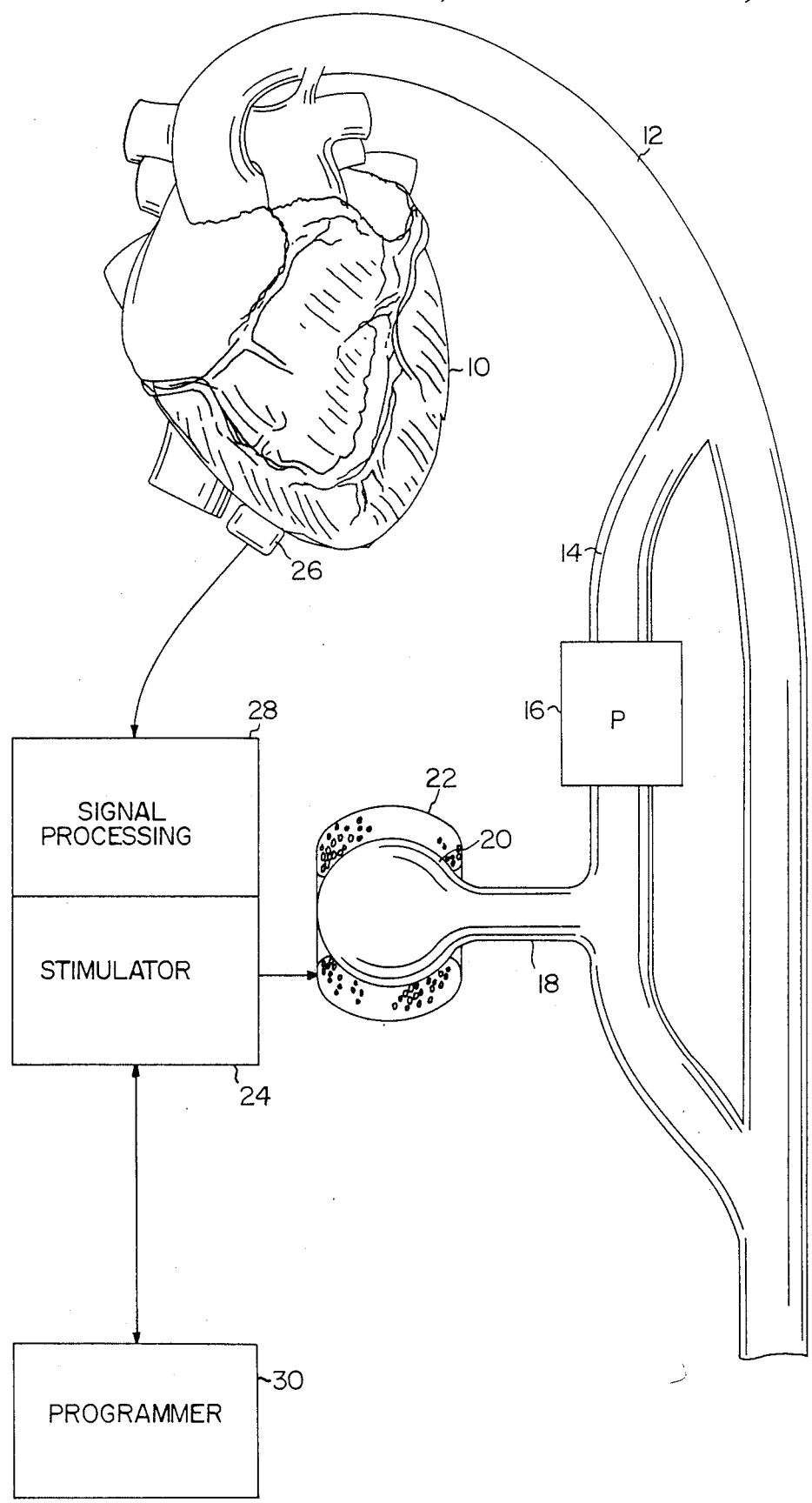

CIRCULATORY ASSIST DEVICE

BACKGROUND OF THE INVENTION

Field of the Invention

This invention relates to medical devices for assisting natural organs in providing blood flow.

The failure of the heart to provide sufficient blood flow is a seriously debilitating problem with symptoms ranging from shortness of breath or swollen limbs to total confinement in bed. In extreme cases, it can result in death. While some forms of heart disease have declined and have been controlled through other therapies, heart failure is a growing problem.

The more serious cases of heart failure have been treated by total replacement of the heart. Transplants of human hearts have saved some patients threatened with death from heart failure. Of course, a heart transplant is a drastic operation with considerable risk. Also, the supply of donor hearts is very limited and cannot meet demand.

Much research has been done in attempting to develop an artificial heart that can replace the human heart in such serious cases. Currently, the artificial heart is in use as a temporary pump pending the location of a human heart for transplant.

A less intrusive method of providing sufficient blood flow is to assist the patient's heart in its pumping process. In this way, there is no risk of rejection and other problems that accompany a heart transplant. Various assist methods have been tried. One train of research has used transformed skeletal muscle to provide the power for the assist. For example, Dr. Ray C.-J. Chiu's book entitled *Biomechanical Cardiac Assist* illustrates a bypass in the aorta. To this bypass is attached a pouch surrounded by skeletal tissue. The skeletal tissue is stimulated by an electrical implantable tissue stimulator. The heart's beating is sensed and the properly conditioned skeletal muscle is pulsed to help in moving blood through the aorta. Considerable research has been done in determining proper muscle choice, such as latissimus dorsi, to use in such an assist.

Another train of development involves the use of mechanical pumps for moving blood. For example, the Biomedicus pump has been used for moving blood through the patient.

One drawback of these continuous power sources is that they lack pulsatility. In the literature, it is urged that a pulsatile system provides a more physiologic flow of blood.

What is needed is a system with a pumping configuration powerful enough to provide sufficient blood flow, while also providing the pulsatility which is believed necessary for the proper end organ perfusion.

SUMMARY OF THE INVENTION

Devices constructed according to the present invention assist blood flow by first providing a continuous flow pump which moves blood in a vessel in assistance of the heart, and second by providing pulses to the blood moving in the vessel to more physiologically simulate natural heart activity.

In the preferred embodiment, a centrifical pump moves blood through a vessel such as the aorta without interruption. Skeletal muscles such as the latissimus dorsi is then mounted for applying a pulse to the flow of blood. This can be done by mounting it on a bypass around the aorta, attachment to a pouch in fluid communication with the aorta, or even by mounting directly on the aorta itself. The muscle is electrically stimulated by a pacemaker-like device. Contraction of the skeletal muscle squeezes the vessel and changes pressure, therefore applying a pulse to the flow within the vessel.

A tissue stimulator is provided for stimulating the skeletal muscle so that it contracts to provide the pulse which is timed properly with respect to the patient's own heartbeat.

Preferably, a sensor is provided which senses contraction of the heart. The stimulation of the skeletal muscle is then timed so as to properly assist the heart and provide a physiologic pulsatile blood flow.

BRIEF DESCRIPTION OF THE DRAWINGS

FIG. 1 is a schematic drawing illustrating the system of the present invention.

DETAILED DESCRIPTION OF THE PREFERRED EMBODIMENT

A system of the present invention is illustrated in FIG. 1 where heart 10 pumps blood through descending aorta 12.

In this particular embodiment, a bypass 14 is fluid-connected to a vessel such as aorta 12 so that a portion of blood pumped by heart 10 passes through bypass 14.

In line with bypass 14 is pump 16, which is a continuous pump.

Pump 16 is preferably a centrifical pump. Examples of prior art devices usable in such an environment are disclosed in U.S. Pat. No. 4,652,265 to McDougall, issued Mar. 24, 1987, and U.S. Pat. No. 4,105,016 to Donovan, Jr., issued Aug. 8, 1978.

A shunt 18 is connected for flow of fluid to bypass 14. Shunt 18 is open to pouch 20. Various prior art methods for constructing pouch 20 may be used as is well known in the literature. Surrounding pouch 20 is natural muscle 22. In the preferred embodiment, this is skeletal muscle such as latissimus dorsi which has been transformed and trained to contract in the proper manner for pulsatile action upon the pouch 20. The method of training is taught in U.S. Pat. No. 4,411,268 to Cox, issued Oct. 25, 1983. For background on use of latissimus dorsi muscle, see the volume by Chiu, cited above.

Various other configurations may be used to mount muscle 22, rather than pouch 20. For example, the prior art teaches mounting muscle 22 directly on bypass 14.

A tissue stimulator 24 is electrically connected to muscle 22 by known prior art methods to provide a stimulating signal for contraction of muscle 22.

Various prior art stimulators, such as Medtronic Itrel ® stimulators, may be used to provide the muscle stimulation.

In the illustrated embodiment, a sensor 26 is provided which senses heart contraction, preferably by electrically sensing depolarization of heart muscle. Stimulator 24 contains signal processing circuitry 28 which interfaces with a signal sensor 26 and indicates to stimulator 24 that a heartbeat has occurred. Stimulator 24 includes circuitry to stimulate muscle 22 so as to provide pulsatility in rhythm with natural heart 10. Of course, when no heart activity from heart 10 is sensed, stimulator 24 may be timed to provide a regular pulsatility.

Stimulator 24 is connected by telemetry to extracorporeal programmer 30. Using known prior art methods, programmer 30 can set parameters from outside the patient. For example, the delay between a heartbeat and a counter-pulse stimulation may be adjusted. It also can program stimulator 24 for concurrent stimulation as the heart beats.

In operation, the system involves pump 16 running at a continuous rate so that blood is flowing through bypass 14 in a continuous manner to assist natural flow out of heart 10 through aorta 12. In order to provide the pulsatility desired for proper perfusion through all parts of the body, stimulator 24 senses each contraction of heart 10. Stimulator 24 then stimulates muscle 22 which squeezes pouch 20. This forces blood through shunt 18 and along through bypass 14. When muscle 22 relaxes, pouch 20 opens and is refilled with blood through shunt 18 from bypass 14.

In this manner, the continual pumping pressure is provided by pump 16 and not through muscle power. Muscle power is employed for the task of providing pulsatility.

By providing the basic pumping pressure from mechanical pump 16, the system according to the present invention results in less muscle fatigue to skeletal muscle 22. In this way, muscle 22 may more efficiently provide pulsatility when there is not a basic pumping mechanism.

While the invention is illustrated in terms of particular embodiments, it is understood that those skilled in the art may employ this invention in combination with other structures for cardiac assist.

What is claimed is:

1. A device for assisting cardiac output comprising:
   implantable pump means for providing continuous pumping of blood through a blood vessel; and
   means for providing pulsatility in the flow of blood provided by the continuous pump means.

2. The device of claim 1 wherein the means for providing pulsatility includes skeletal muscle for contracting to provide the pulsatility and an electrical tissue stimulator for stimulating the skeletal muscle to contract.

3. The device of claim 2 further comprising a sensor electrically connected to the stimulator and means within the stimulator for timing, based upon signals from the sensor, for stimulation of the muscle.

4. The device of claim 2 further comprising internal means in the stimulator for storing parameters upon which decisions are made to stimulate skeletal muscle and an extracorporeal programmer for communicating with the stimulator by telemetry for storing parameters within the stimulator.

5. A method of assisting output of the heart comprising:
   providing a continuous output implantable pump for moving blood through a vessel;
   applying pulses to the blood flowing in the vessel to simulate the pulsatility of a naturally pumping heart.

6. The method of claim 5 wherein the applying of pulses includes:
   supplying an electrical signal to contract natural skeletal muscle to supply the pulse to the moving blood.

7. A method of assisting the output of a heart comprising:
   providing a continuous pump to move blood through a human vessel;
   sensing contraction of the heart and providing a signal indicative of a heart contraction;
   providing a pulse to blood moving in the vessel based upon the signal from the sensor.

8. The device of claim 2 further comprising:
   means in the tissue stimulator for receiving a delay parameter telemetered extracorporeally;
   means for storing the delay parameter;
   means for sensing a heartbeat; and
   means for determining, based upon the stored delay parameter, a delay time between heartbeat and stimulation of the muscle.

9. A method of assisting the output of the heart comprising:
   providing a continuous pump to move blood through a human vessel;
   providing means for supplying pulsatility to blood flow through flexing a natural skeletal muscle;
   providing means for stimulating the skeletal muscle for flexing the muscle;
   means for sensing the contraction of the heart and for providing a signal indicative of the heart contraction;
   means for extracorporeally telemetering to the means for stimulating a delay signal; and
   sensing a contraction of the heart and, based upon the delay signal, and providing a stimulating pulse to the muscle.

* * * * *